United States Patent
Zhang et al.

(10) Patent No.: US 9,891,584 B2
(45) Date of Patent: Feb. 13, 2018

(54) COHERENT DIFFRACTIVE IMAGING WITH ARBITRARY ANGLE OF INCIDENCE

(71) Applicants: Bosheng Zhang, Pleasanton, CA (US); Matthew D. Seaberg, San Mateo, CA (US); Daniel E. Adams, Boulder, CO (US); Henry C. Kapteyn, Boulder, CO (US); Margaret M. Murnane, Boulder, CO (US)

(72) Inventors: Bosheng Zhang, Pleasanton, CA (US); Matthew D. Seaberg, San Mateo, CA (US); Daniel E. Adams, Boulder, CO (US); Henry C. Kapteyn, Boulder, CO (US); Margaret M. Murnane, Boulder, CO (US)

(73) Assignee: The Regents of the University of Colorado, a body, Denver, CO (US)

( * ) Notice: Subject to any disclaimer, the term of this patent is extended or adjusted under 35 U.S.C. 154(b) by 362 days.

(21) Appl. No.: 14/839,738

(22) Filed: Aug. 28, 2015

(65) Prior Publication Data
US 2016/0187849 A1 Jun. 30, 2016

Related U.S. Application Data

(60) Provisional application No. 62/043,132, filed on Aug. 28, 2014.

(51) Int. Cl.
*H04N 19/124* (2014.01)
*G01N 23/20* (2006.01)
(Continued)

(52) U.S. Cl.
CPC ....... *G03H 1/0443* (2013.01); *G01N 23/2055* (2013.01); *G02B 21/0016* (2013.01);
(Continued)

(58) Field of Classification Search
CPC .......... G01N 21/4788; G01N 23/2055; G01N 2223/611; G01N 23/20; G03F 1/84; G03F 7/70625
See application file for complete search history.

(56) References Cited

U.S. PATENT DOCUMENTS 6,411,406 B1 6/2002 Kreuzer
2012/0105744 A1* 5/2012 Maiden ................. G02B 21/02
349/2
(Continued)

OTHER PUBLICATIONS

Harada et al., Phase Imaging of Extreme-Ultraviolet Mask Using Coherent Extreme-Ultraviolet Scatterometry Microscope, Japanese Journal of Applied Physics 52, 2013.
(Continued)

*Primary Examiner* — Obafemi Sosanya
(74) *Attorney, Agent, or Firm* — Macheledt Bales LLP; Jennifer L. Bales (57) ABSTRACT

Apparatus and methods for coherent diffractive imaging with arbitrary angle of illumination incidence utilize a method of fast remapping of a detected diffraction intensity pattern from a detector pixel array (initial grid) to a uniform spatial frequency grid (final grid) chosen to allow for FFT on the remapped pattern. This is accomplished by remapping the initial grid to an intermediate grid chosen to result in a final grid that is linear in spatial frequency. The initial grid is remapped (generally by interpolation) to the intermediate grid that is calculated to correspond to the final grid. In general, the initial grid (x,y) is uniform in space, the intermediate grid $(\tilde{x},\tilde{y})$ is non-uniform in spatial frequency, and the final grid $(f_x,f_y)$ is uniform in spatial frequency.

22 Claims, 10 Drawing Sheets

(51) Int. Cl.
- *G01N 23/2055* (2018.01)
- *G03H 1/04* (2006.01)
- *G02B 21/00* (2006.01)
- *G02B 27/42* (2006.01)
- *G03H 1/16* (2006.01)
- *G03F 7/20* (2006.01)
- *G03F 1/84* (2012.01)
- *G01N 23/205* (2018.01)
- *H04N 19/109* (2014.01)
- *G03H 1/00* (2006.01)
- *G01N 21/47* (2006.01)
- *G01N 21/956* (2006.01)

(52) U.S. Cl.
CPC ........... *G02B 27/4205* (2013.01); *G03F 1/84* (2013.01); *G03F 7/70625* (2013.01); *G03H 1/0465* (2013.01); *G03H 1/16* (2013.01); *G01N 21/4788* (2013.01); *G01N 2021/95676* (2013.01); *G01N 2223/611* (2013.01); *G03H 2001/005* (2013.01); *G03H 2001/045* (2013.01); *G03H 2001/0445* (2013.01); *G03H 2001/0456* (2013.01)

(56) References Cited

U.S. PATENT DOCUMENTS

2015/0108352 A1* 4/2015 Maiden .................. G01N 23/20
250/336.1
2016/0154301 A1* 6/2016 Ekinci ....................... G03F 1/84
250/372

OTHER PUBLICATIONS

Gardener et al., High numerical aperture reflection mode coherent diffraction microscopy using off-axis apertured illumination, Optics Express, vol. 20, No. 16, Aug. 13, 2012.

Seaberg et al., Tabletop nanometer extreme ultraviolet imaging in an extended reflection mode using coherent Fresnel ptychography, Optica vol. 1 No. 1, Jul. 2014.

* cited by examiner

COHERENT DIFFRACTIVE IMAGING WITH ARBITRARY ANGLE OF INCIDENCE

BACKGROUND OF THE INVENTION

Field of the Invention

The present invention relates to microscopy and other forms of imaging using coherent light. In particular, the present invention relates to coherent diffractive imaging (CDI) with an arbitrary angle of incidence.

Discussion of Related Art

Figure 1A:
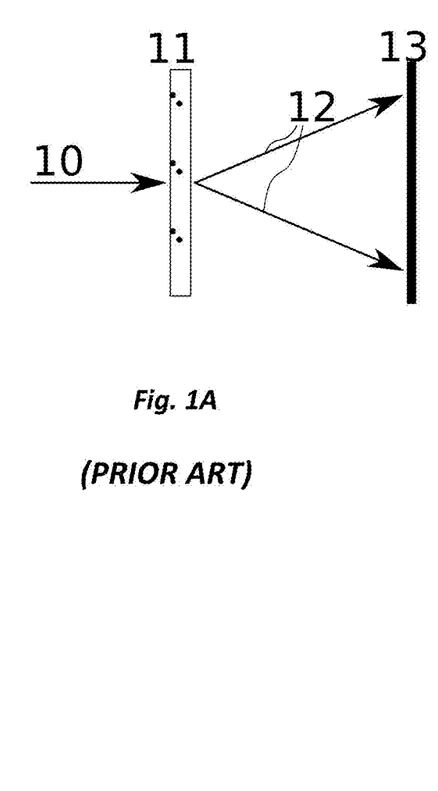
FIGS. 1A-1C (Prior Art) are schematic diagrams illustrating conventional configurations of CDI.

Coherent diffractive imaging (CDI), for example ptychography, is an emerging technique that enables wavelength- and diffraction-limited imaging. FIG. 1A (Prior Art) shows a conventional 2-dimensional transmission CDI system, where incident radiation 10 illuminates object 11 with a normal incidence, and transmitted scattering field 12 is measured on detector 13.

Figure 1B:
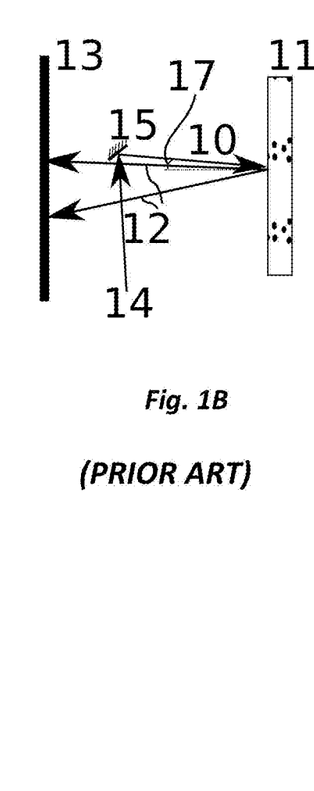

FIG. 1B (Prior Art) shows a conventional 2-dimensional reflection CDI, where the incident radiation before reflection 14 reflects off of mirror 15 as incident radiation 10 and illuminates object 11 with near-normal incidence (the angle of incidence 17 $\theta_i$ is close to 0 degrees).

Figure 1C:
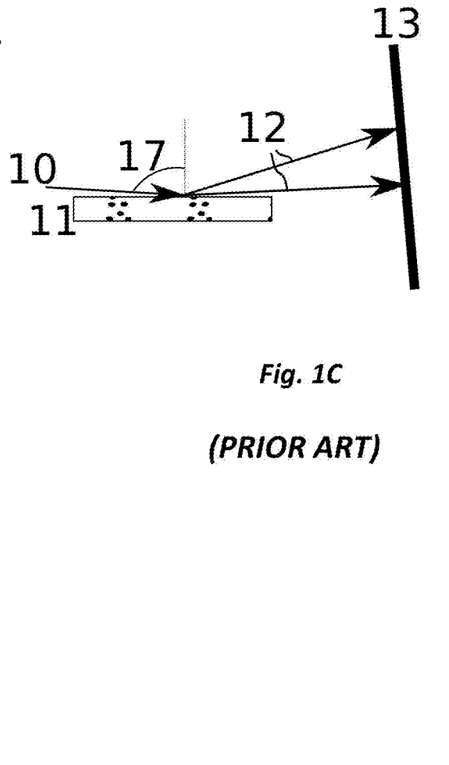

FIG. 1C shows CDI in a reflection geometry with grazing incidence (the angle of incidence 17 $\theta_i$ is close to 90 degrees). With non-normal incidence, there is apparent distortion in the measured diffraction pattern, and a method that corrects the distortion was introduced in prior art (see, for example, Gardner, D. F. et al., Opt. Express 20, 19050-9, 2012). In this method, the spatial frequency is calculated for each position on the detector, and then the scatter pattern is remapped from the calculated non-uniform frequency grid to a uniform frequency grid. This method is time consuming because it requires remapping from a non-uniform grid to a uniform grid, which typically involves triangulation.

The fact that conventional CDI is limited to the above configurations brings several disadvantages: 1) it limits the freedom of the imaging geometry; 2) for reflection CDI, it results in a narrow range of scattering available for detection, leading to low resolution in the reconstructed image; 3) the reflectivity of objects might be low at near-zero degrees incidence. A need remains in the art for methods and apparatus to enable CDI with arbitrary angle of incidence and efficient computation.

SUMMARY

An object of the present invention is to provide apparatus and methods for efficient CDI with arbitrary angle of incidence.

The invention includes the development of practical techniques for microscopy and other forms of imaging using coherent light. In particular, the use of coherent diffractive imaging techniques in conjunction with short-wavelength deep-UV, vacuum ultraviolet (VUV), extreme ultraviolet (EUV), and soft x-ray (SXR) sources allows for new methodologies for diffraction-limited imaging, with the numerical aperture depending only on the solid-angle of collected light. In the VUV-EUV-SXR regions of the spectrum, obviating the need for an imaging optic dramatically improves the prospects for imaging with high-NA; i.e. near wavelength-limited resolution.

Embodiments of the present invention provide a fast numerical method for processing the measured scattering pattern, so it is amenable for use with Fast Fourier transform (FFT) in the reconstruction of the image.

Embodiments of the present invention provide methods and apparatus to image objects at arbitrary angles of incidence both in reflection and transmission.

Embodiments of the present invention provide methods and apparatus to image objects with multi-wavelength illumination at an arbitrary angle of choice.

Embodiments of the present invention provide methods and apparatus to image a dynamic process with high NA.

A method of fast remapping of a detected diffraction intensity from a detector pixel array (initial grid) to a uniform spatial frequency grid (final grid) allows for FFT on the final grid. This is accomplished by remapping the initial grid to an intermediate grid chosen to result in a final grid that is linear in spatial frequency. The initial grid is remapped (generally by interpolation) to the intermediate grid that is calculated to correspond to the final grid. In general, the initial grid (x,y) is uniform in space, the intermediate grid ($\tilde{x},\tilde{y}$) is non-uniform in spatial frequency, and the final grid ($f_x,f_y$) is uniform in spatial frequency.

The present invention may be used in image reconstruction for any high NA diffractive imaging configuration, including a) the normal incidence configuration and b) the non-normal incidence configurations for which the remapping includes what is termed "tilted plane correction" in prior art (Gardner, D. F. et al., Opt. Express 20, 19050-9, 2012).

An imaging instrument capable of imaging samples at arbitrary angle of incidence consists of a) a radiation source; b) focusing optic(s) to condense the light onto the sample; and c) scanning ptychography. This instrument could have a light source from high-order harmonic upconversion of a driving laser. It could operate in a transmission mode configuration or a reflection mode configuration.

The instrument could use a vacuum iris far upstream of the focusing element, instead of positioning it close to the sample, to create well-confined illumination without decreasing the working distance of the microscope.

The focusing optic might be an off-axis or grazing incidence focusing optic (typically an ellipsoidal mirror or a toroidal mirror). The focusing optics may employ a concave EUV multilayer mirror.

The high-order harmonic conversion can be of any polarization state, including linear, circular and elliptical polarization, for magnetic imaging. Imaging can be done performing hyperspectral ptychography imaging of samples at arbitrary incidence angle using a comb of high-order harmonics, or other multi-wavelength illumination.

A comb of harmonics may be used for hyperspectral imaging

The illumination spectrum may be tailored for coherent imaging using a combination of high-harmonic generation, spectral filters such as thin-film EUV filters, a zero-dispersion stretcher with spectrum modulation in the spectrum plane, and multilayer or grazing incidence reflection to obtain an optimum spectrum for illumination, which may include one or more wavelengths or a well-defined continuous bandwidth.

A method of using ptychography obtains information on the illumination wavefront at the sample, then subsequently uses keyhole imaging that makes use of the obtained wavefront.

Stroboscopic imaging uses scanning reflection mode ptychography.

BRIEF DESCRIPTION OF THE DRAWINGS

FIG. 1A (Prior Art) shows CDI in a transmission geometry. FIG. 1B (Prior Art) shows CDI in a reflection geometry with near-normal incidence. FIG. 1C (Prior Art) shows CDI in a reflection geometry with grazing incidence.

FIG. 5A uses an ellipsoidal mirror as focusing optics. FIG. 5B uses an EUV mirror as focusing optics. FIG. 5C is a transmissive configuration.

DETAILED DESCRIPTION OF THE INVENTION

The following table of elements and reference numbers is provided for convenience.

- 10 Incident radiation
- 11 Object
- 12 Scattering field
- 13 Detector
- 14 Incident radiation before reflection
- 15 Mirror
- 17 Angle of incidence or reflection $\theta_i$
- 20 Incident radiation (transmission geometry)
- 21 Incident radiation (reflection geometry)
- 22 Object
- 24 Diffraction intensity
- 25 Detector
- 26 Diffraction intensity pattern detected
- 27 Initial (detector) grid (generally spatially uniform)
- 28 Remapped pattern on grid 29
- 29 Intermediate grid (chosen to result in uniform spatial frequency grid 202)
- 34 Step of remapping according to the present invention
- 35 Slow conventional remapping
- 44 Fourier transform magnitude on the detector grid 27
- 48 The step of calculating the Fourier transform magnitude
- 202 Final grid (generally uniform spatial frequency)
- 204 Prior art step of converting from detector grid 27 to a non-uniform spatial frequency grid 302
- 206 Step of calculating intermediate grid 29 from final grid 202
- 211 The distance from the sample to the detector plane $z_{ds}$
- 212 Diffraction field magnitude calculated
- 302 Prior art non-uniform spatial frequency grid
- 501 Driving laser beam
- 502 Medium
- 503 Residual driving beam
- 504 Vacuum iris -continued

Figure 2A:
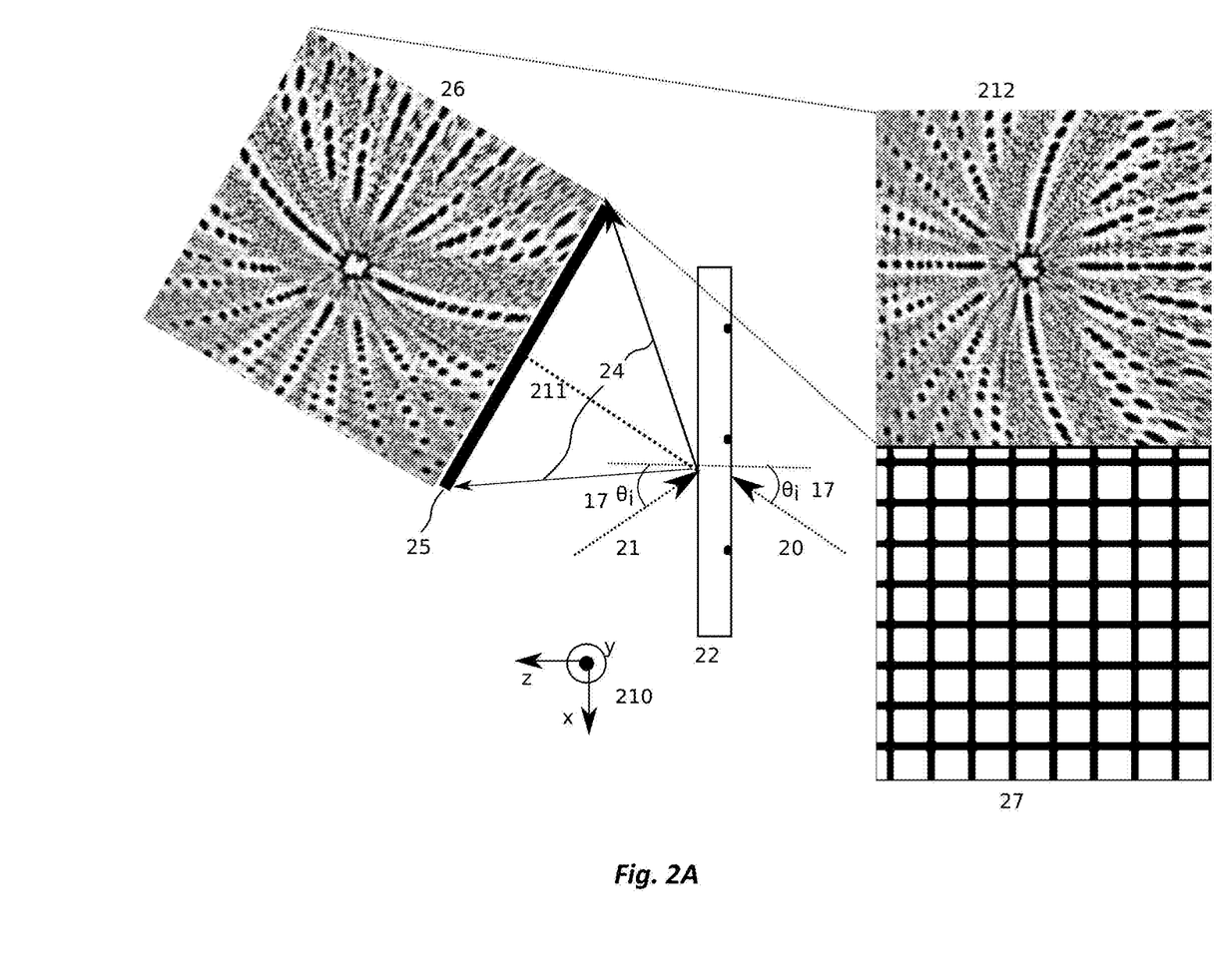
FIG. 2A is a schematic block diagram illustrating an imaging device according to the present invention for CDI at arbitrary angle of incidence captured with a pixel array detector, generally comprising a spatially uniform grid.
Figure 2B:
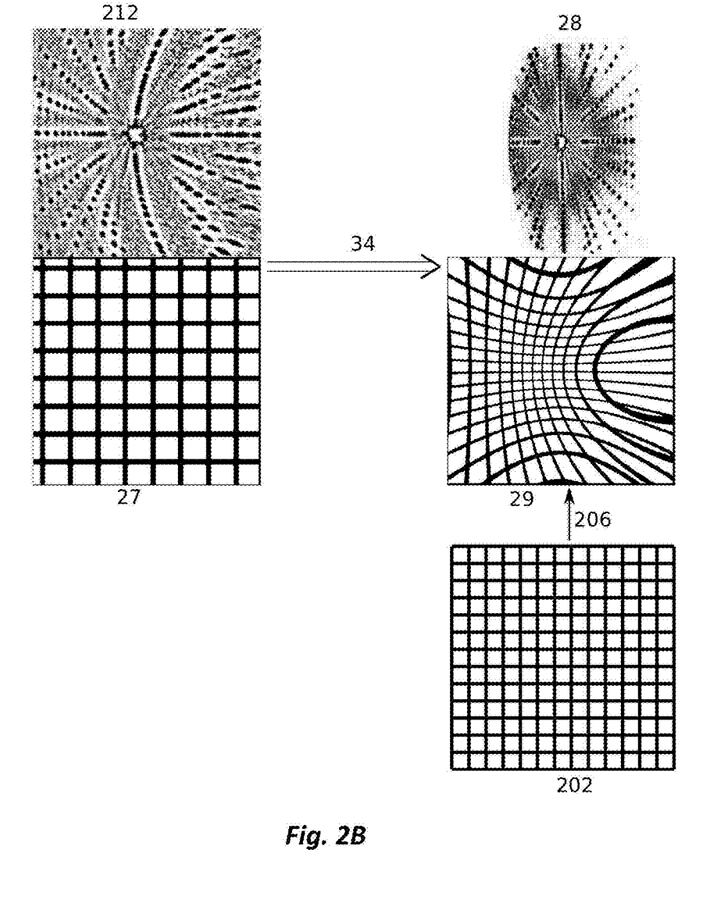
FIG. 2B is a schematic block diagram illustrating the process of fast remapping from the detector pixel array to a final (generally uniform spatial frequency) grid.

- 505 Optics
- 506 Beam after optics 505
- 507 Off-axis focusing optics
- 508 Focusing mirror
- 509 Focused beam
- 510 Sample
- 512 Diffracted field
- 513 Detector FIG. 2A is a schematic block diagram illustrating an imaging device according to the present invention for CDI at arbitrary angle of incidence 17 captured with a detector pixel array 25, generally comprising a spatially uniform grid 27. FIG. 2B is a schematic block diagram illustrating the process of fast remapping 34 from the detector pixel array grid 27 to a final (generally uniform spatial frequency) grid 202.

FIG. 2A illustrates coherent diffraction imaging (CDI) with arbitrary angle of incidence $\theta_i$ 17. Object 22 is illuminated by transmitted incident beam 20 or reflected incident beam 21. Diffracted intensity 24 is measured by detector 25. Detector 25 is generally a uniform array of pixels, so initial grid 27 is uniform in space. Diffraction field magnitude 212 is based on diffraction intensity 26.

FIG. 2B illustrates a method of performing a remapping 34 of the diffraction field magnitude 212, from an initial uniform detector grid 27, to an intermediate (non-uniform spatial) grid 29. The intermediate grid 29 is calculated from the final (uniform spatial frequency) grid 202 in step 206. The remapped pattern 28 is then amenable to be used with Fast Fourier transform in CDI reconstructions.

Figure 3:
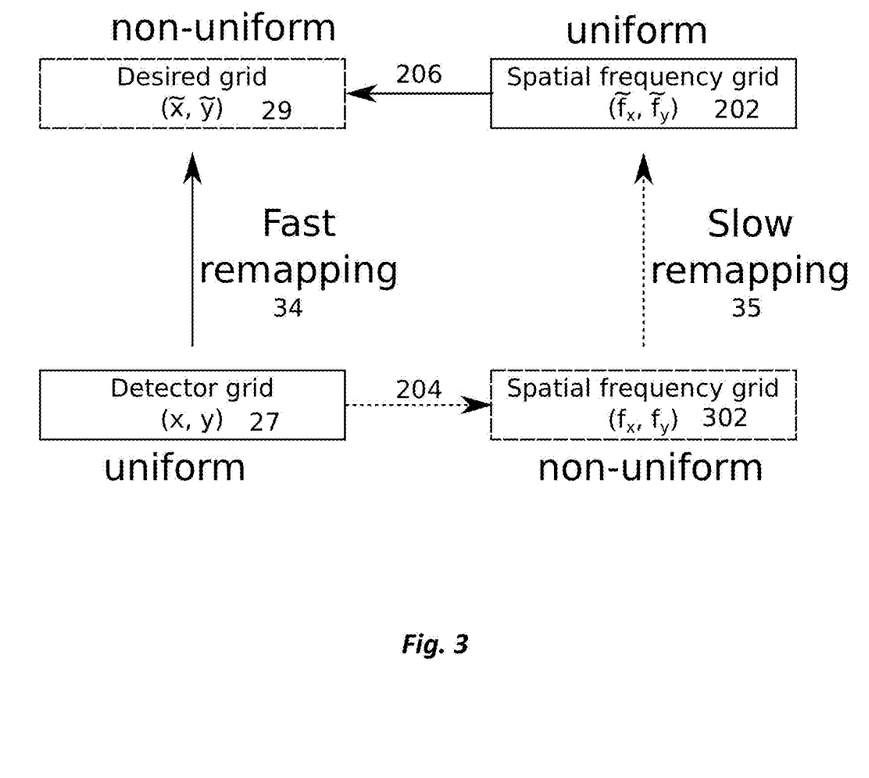
FIG. 3 is a flow chart contrasting a remapping algorithm according to the present invention with the prior art remapping algorithm.

FIG. 3 compares the conventional slow remapping approach with the fast remapping approach of the current invention. The goal is to obtain the Fourier transform magnitude from the uniform detector grid (x,y) 27 to a chosen uniform spatial frequency grid $(f_x,f_y)$ 202.

In the prior art, first the spatial frequency grid $(f_x,f_y)$ 302 that corresponds to the detector grid is calculated. $(f_x,f_y)$ 302 turns out to be non-uniform due to the nonlinear relationship with (x,y) 27. Then the Fourier transform magnitude is remapped from non-uniform grid $(f_x,f_y)$ 302 to uniform grid $(\tilde{f}_x,\tilde{f}_y)$ 202, which is a time consuming process, because remapping from a non-uniform to a uniform grid typically involves triangulation.

In the implementation of the present invention, we first calculate the intermediate non-uniform spatial grid $(\tilde{x},\tilde{y})$ 29 that corresponds to eventual desired grid $(\tilde{f}_x,\tilde{f}_y)$ 202, in step 206. Then the Fourier transform magnitude 44 is remapped from initial uniform grid (x,y) 27 to intermediate non-uniform grid $(\tilde{x},\tilde{y})$ 29 in step 34. Remapping from a uniform grid to a non-uniform one, instead of the other way around, is fast. The key is to choose an appropriate coordinate transform that enables the eventual usage of Fast Fourier transform, similar to what has been done in holographic microscopes (for example, see Kreuzer, U.S. Pat. No. 6,411, 406 B1).

Figure 4:
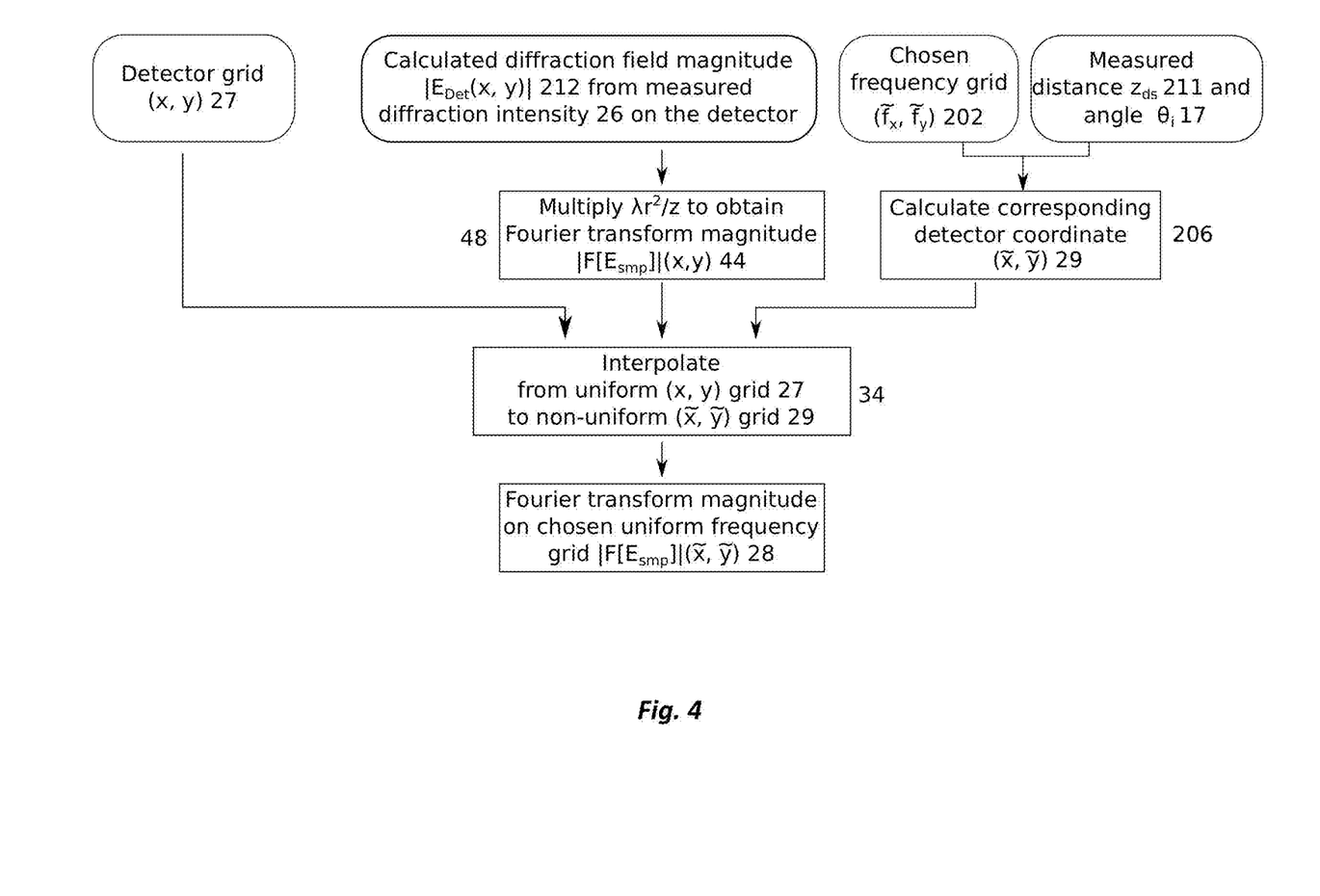
FIG. 4 is a flow diagram illustrating the remapping algorithm according to the present invention in more detail.

FIG. 4 shows an example of a detailed procedure to perform the fast remapping. Inputs to the process are initial spatial grid 27, calculated diffraction field magnitude 212, final spatial frequency grid 202, measured distance $z_{ds}$ 211, and illumination incidence angle $\theta_i$ 17. The diffraction field magnitude 212 can be calculated from the directly measured diffraction intensity 26: First, certain preprocessing is performed, such as subtracting non-zero background that is not from the diffraction field, and dividing the cosine of the angle between incident photon direction and the detector normal direction; Secondly, square root is taken to convert from processed intensity (field magnitude squared), to field magnitude 212.

Without losing generality, any coordinate system may be chosen but for this example we select one for which the xy-plane is on the sample plane and for which the xz-plane is parallel to the incident wave vector $\vec{k}_0$, such as coordinate system 210 in FIG. 2A. Then any point on the sample plane is denoted as $\vec{r}'=(x', y', z'=0)$, and $\vec{k}_0$ can be written as $\vec{k}_0=(k_{0x}, k_{0y}, k_{0z})=(\sin\theta_i, 0, \cos\theta_i)$. We assume that $z=z(x,y)$ is the z coordinate for any point on the detector grid (x,y) 27. In some notations, z is not explicitly written out since it can be determined from x and y, for example, $E_{Det}(x,y)$ means the same as $E_{Det}(x, y, z)$. Then at point on the detector $\vec{r}=(x, y, z(x,y))$, the diffracted field on the detector can be related to the exit surface wave at the sample $E_{Smp}(x', y')$ with the first Rayleigh-Sommerfeld integral, which is:

$$E_{Det}(x, y, z) = \int\int_\Sigma dx'dy' [E_{Smp}(x', y') e^{i(k_{0x}x'+k_{0y}y')}] \frac{1}{i\lambda} \frac{e^{ikR}}{R} \frac{z}{R}\left(1 - \frac{1}{ikR}\right) \quad (1)$$

where $\Sigma$ is the sample plane, is the wavelength of the incident radiation, $k=2\pi/\lambda$ is the angular wave number, $R=\sqrt{(x-x')^2+(y-y')^2+z^2}$ is the distance from a sample point (x', y', 0) to (x, y, z). Notice that we explicitly write out the linear phase in the field for the non-normal incidence case. Assuming $|\vec{r}|>>\max[|\vec{r}'|, \lambda]$ and the far field condition $|\vec{r}|>>D^2/\lambda$, (D is the physical size of the sample) then equation (1) can be approximated with a 2D Fourier transform:

$$E_{Det}(x, y, z) = \frac{e^{ikr}}{i\lambda} \frac{z}{r^2} F[E_{Smp}]|_{f_x,f_y} \quad (2)$$

where:

$$f_x = \frac{1}{\lambda}\left(\frac{x}{\sqrt{x^2+y^2+z^2}} - \hat{k}_{0x}\right) \quad (3)$$

$$f_y = \frac{1}{\lambda}\left(\frac{y}{\sqrt{x^2+y^2+z^2}} - \hat{k}_{0y}\right) \quad (4)$$

and $$\hat{k}_0 = \frac{\lambda}{2\pi}\vec{k}_0$$

is the normalized incident wave vector.

Assume $z_{ds}$ is the distance from the sample to the detector plane 211, $\vec{n}_{det}$ is the normal vector of the detector plane, then any point $\vec{r}'=(x, y, z)$ on the detector satisfy:

$$\vec{n}_{det} \cdot \vec{r} = z_{ds} \quad (5)$$

With equation (2), from the measured diffraction field magnitude on detector $|E_{Det}(x, y, z)|$ 212, the magnitude of the Fourier transform of the sample-plane E field $|F[E_{Smp}]|_{f_x,f_y}|$ 44 can be calculated (step 48) using $$|F[E_{Smp}]|_{f_x,f_y}| = \frac{\lambda r^2}{z}|E_{Det}(x, y, z)| \quad (6)$$

To allow for the use of fast Fourier transform (FFT) in CDI reconstructions, we need to use the E-field Fourier transform magnitude on a uniform grid of frequencies $(\tilde{f}_x,\tilde{f}_y)$, instead of on a uniform grid of detector pixel coordinates which correspond to a non-uniform grid of frequencies $(f_x,f_y)$. The most straightforward way to obtain $|E(\tilde{f}_x,\tilde{f}_y)|$ from $|E(x, y, z)|$ is as following: first, calculate $(f_x,f_y)$ for all pixel coordinates (x, y, z) using equation (3) and (4), resulting in a non-uniform grid; secondly, interpolate E magnitude from non-uniform $(f_x,f_y)$ grid onto the uniform grid $(\tilde{f}_x,\tilde{f}_y)$. This way is intuitive, but interpolation from a non-uniform to uniform grid is time-consuming as it typically involves triangulation methods. Instead, we use a different and much faster approach. Assume $(\hat{f}_x, \hat{f}_x)=\lambda(\tilde{f}_x,\tilde{f}_y)$ is the chosen uniform frequency grid 202 normalized by $1/\lambda$. First we calculate the coordinates $(\tilde{x},\tilde{y})$ 29 corresponding to the uniform grid $(\tilde{f}_x,\tilde{f}_y)$ of choice 202 from equations (3), (4) and (5) using the measured distance $z_{ds}$ 211 and angle $\theta_i$ 17:

$$\tilde{x} = z_{ds}\frac{1}{\cos\theta_i \cdot \hat{f}_z + \sin\theta_i \cdot \hat{f}_x}\hat{f}_x \quad (7)$$

$$\tilde{y} = z_{ds}\frac{1}{\cos\theta_i \cdot \hat{f}_z + \sin\theta_i \cdot \hat{f}_x}\hat{f}_y \quad (8)$$

where $$\hat{f}_z = \left(\sqrt{1-(\lambda\hat{f}_x+\sin\theta_i)^2-(\lambda\hat{f}_y)^2} - \cos\theta_i\right). \quad (9)$$

Then, in step 34, we interpolate $|F[E_{Smp}]|_{f_x,f_y}|$ 44 from (x,y) 27 onto $(\tilde{x},\tilde{y})$ 29 to obtain Fourier transform magnitude $|F[E_{Smp}]|_{\tilde{f}_x,\tilde{f}_y}|$ 28. Interpolation methods, such as bilinear interpolation and bicubic interpolation or many others, are available to interpolate from a 2D uniform to a 2D non-uniform grid, and are much faster than the previous interpolation method.

In summary, the steps of performing fast reforming 34 are as following:
1. The inputs are: detector grid (x,y) 27, z value for each (x,y) grid point z(x,y), calculated diffraction field magnitude on detector $E_{Det}(x, y, z)$ 212, a given spatial frequency grid $(\tilde{f}_x,\tilde{f}_y)$ 202, and two experiment parameters $\theta_i$ 17 and $z_{ds}$ 211.
2. Calculate the Fourier transform magnitude on the detector grid (x,y) 27: $|F[E_{Smp}](x,y)|$ (or $|F[E_{Smp}]|_{f_x,f_y}|$ as written before) 44 using equation (6). This is step 48.
3. Calculate the desired grid $(\tilde{x},\tilde{y})$ 29 with equation (7). This is step 206.
4. Then interpolate Fourier transform magnitude from detector grid 27 to the desired grid 29. This is step 34.

As seen from equations (7) and (8), the fast remapping is wavelength-independent making it suitable for hyperspectral imaging in which the incident radiation contains multiple wavelengths.

Although the distortion in the diffraction looks more obvious with non-normal incidence, for any diffraction measured with wide collecting angle, or high numerical aperture (NA), even for normal-incidence, it may be advisable to perform the remapping. The remapping results in a better result for any high-NA configuration simply because the spatial-frequency coordinates have a non-linear relationship with the detector pixel coordinates. An alternative to the remapping would be to use a Non-uniform FFT.

Figure 5A:
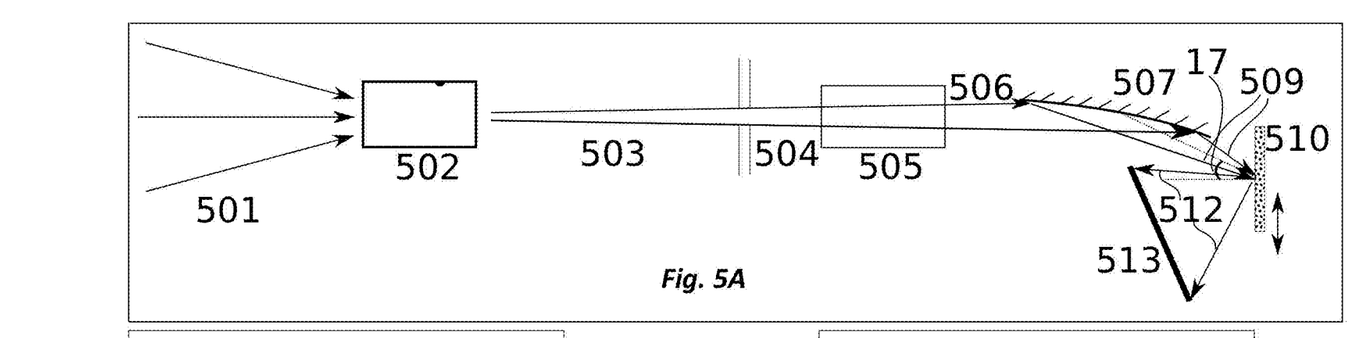
FIGS. 5A-5C are schematic representations of a HHG ptychography microscope in various configurations, used to implement embodiments of the present invention.

FIG. 5A shows one embodiment of a ptychography microscope that can image objects at any angle of incidence, with high harmonic generation (HHG) as the incident radiation source. A driving laser beam 501, such as a Ti:sapphire laser beam, interacts with atoms in the medium 502, and the resulted HHG beam together with the residual driving beam 503 propagated through a vacuum iris with ~1 mm size and far (1 m) upstream from the focusing optics 507 or 508 (see FIG. 5B). The vacuum iris 504 passes the majority of the beam while imprinting a hard edge on the beam shape. Various optional optical elements 505 including spectral filters, rejector mirrors, or multilayer mirrors, may serve to steer the beam, filter out the driving laser, or modify the spectrum of the HHG beam. The HHG beam then is focused to illuminate a small area of the sample 510.

Figure 5B:
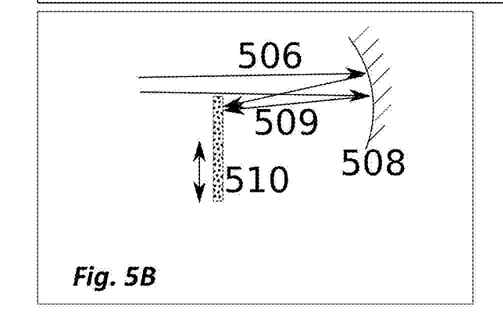
Figure 5C:
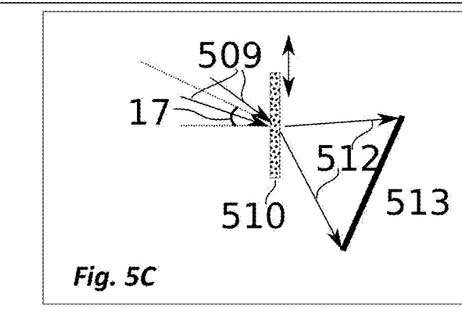

FIG. 5A and FIG. 5B show 2 possible ways of focusing as examples. In FIG. 5A, off-axis optics 507, including an ellipsoidal mirror, or a toroidal mirror, is used to focus the illumination 506; while in FIG. 5B, a mirror at near-normal incidence 508 serves this purpose. It is also possible to use transmissive optics, such as a lens or a Fresnel zone plate to focus the light. The use of off-axis optics 507 typically allows for larger scanning area than near-normal incidence mirrors 508. Elements 505 and focusing optics 507, 508 may include at least one multilayer mirror to select only one harmonic that is more monochromatic than several harmonics. The focused beam 509 then illuminates the sample 510 with an arbitrary angle of incidence $\theta_i$ 17. The scattered light can be measured using either reflection geometry as shown in FIG. 5A, or a transmission geometry as shown in FIG. 5C. The sample is mounted on a multi-axis scan stage (not shown) for ptychography scanning. A pixel array detector 513, for example a CCD or CMOS, is employed to measure the magnitude of the diffracted field 512.

As an example, we used the imaging instrument of the present invention to image a test object, which is composed of titanium of about 30 nm thickness deposited on a silicon wafer. The fast remapping is performed on each diffraction pattern in the ptychography scan, which is composed of approximately 200 diffraction patterns. The fast remapping algorithms is beneficial for practical implementation of the microscope reconstruction step.

Figure 6:
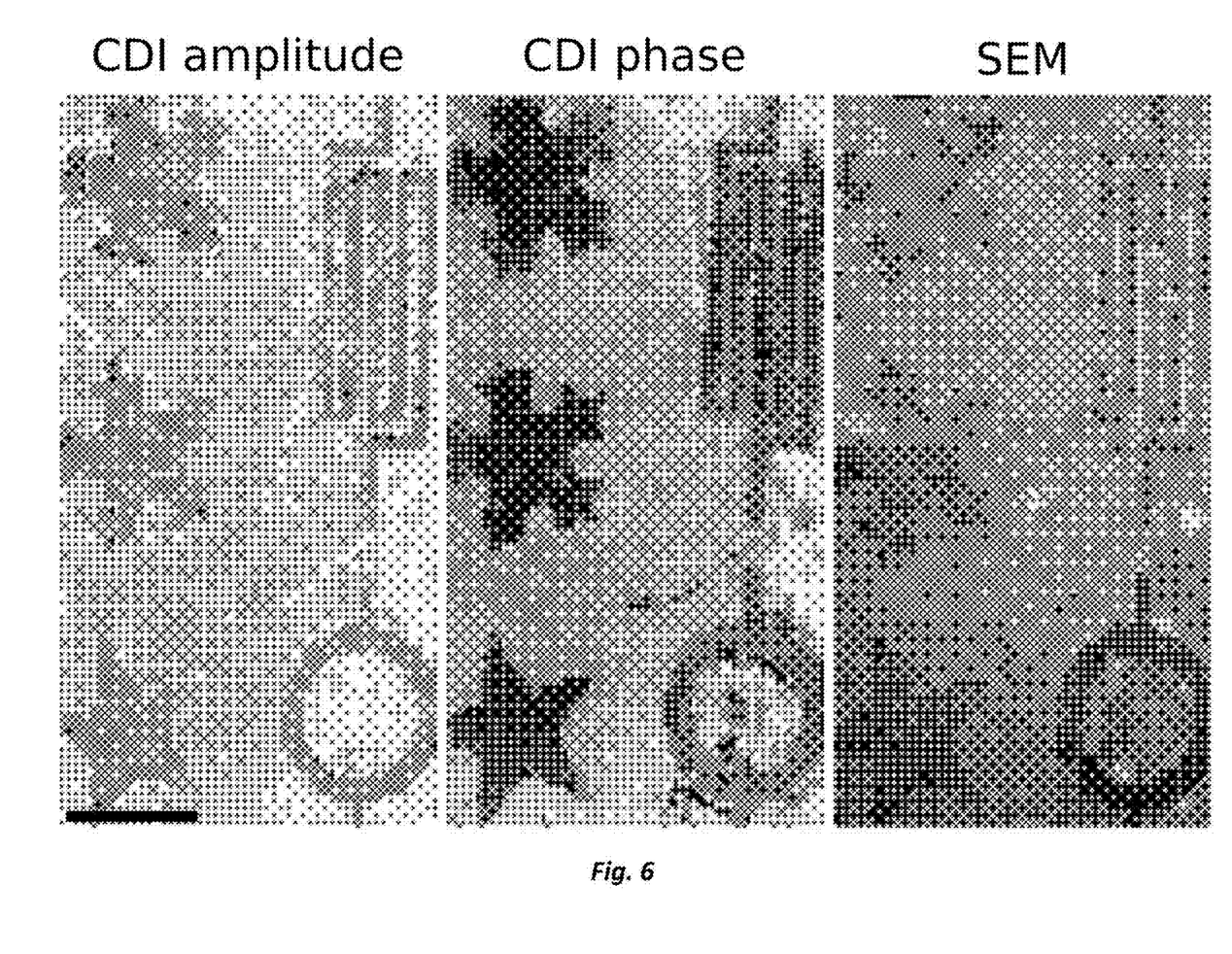
FIG. 6 illustrates amplitude and phase images from a reflection-mode HHG ptychography microscope according the present invention, contrasted with an image from a conventional scanning electron microscope.

FIG. 6 shows the CDI reconstruction of the amplitude and the phase of the sample, compared with a scanning electron microscope image. Amplitude (left) and phase (center) images from a reflection-mode HHG ptychography microscope are compared with an SEM image (right). The black scale bar at the bottom left-hand corner indicates 10 µm. The exposure time for the whole scan takes 1 minute, and the numerical aperture is 0.22 horizontally and 0.39 vertically, supporting a horizontal and vertical half-pitch resolution of 66 nm and 37 nm respectively.

Figure 7:
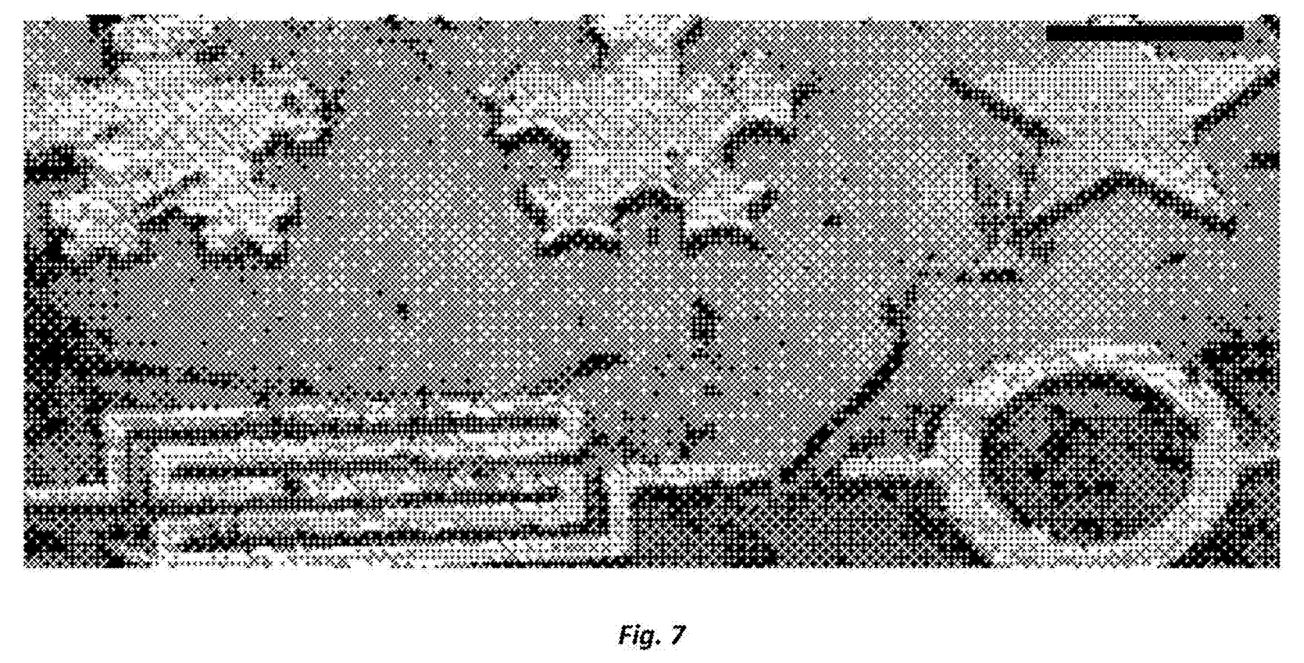
FIG. 7 illustrates height profile calculated from reconstructed phase of FIG. 6.

FIG. 7 shows the calculated height profile from the reconstructed phase of FIG. 6. Again, the black scale bar at the bottom left-hand corner indicates 10 µm.

The microscope according to the invention has potential for applications including inspection of masks for lithography, semiconductor metrology, and general surface profilometry. It also has applications for magnetic imaging.

Figure 8:
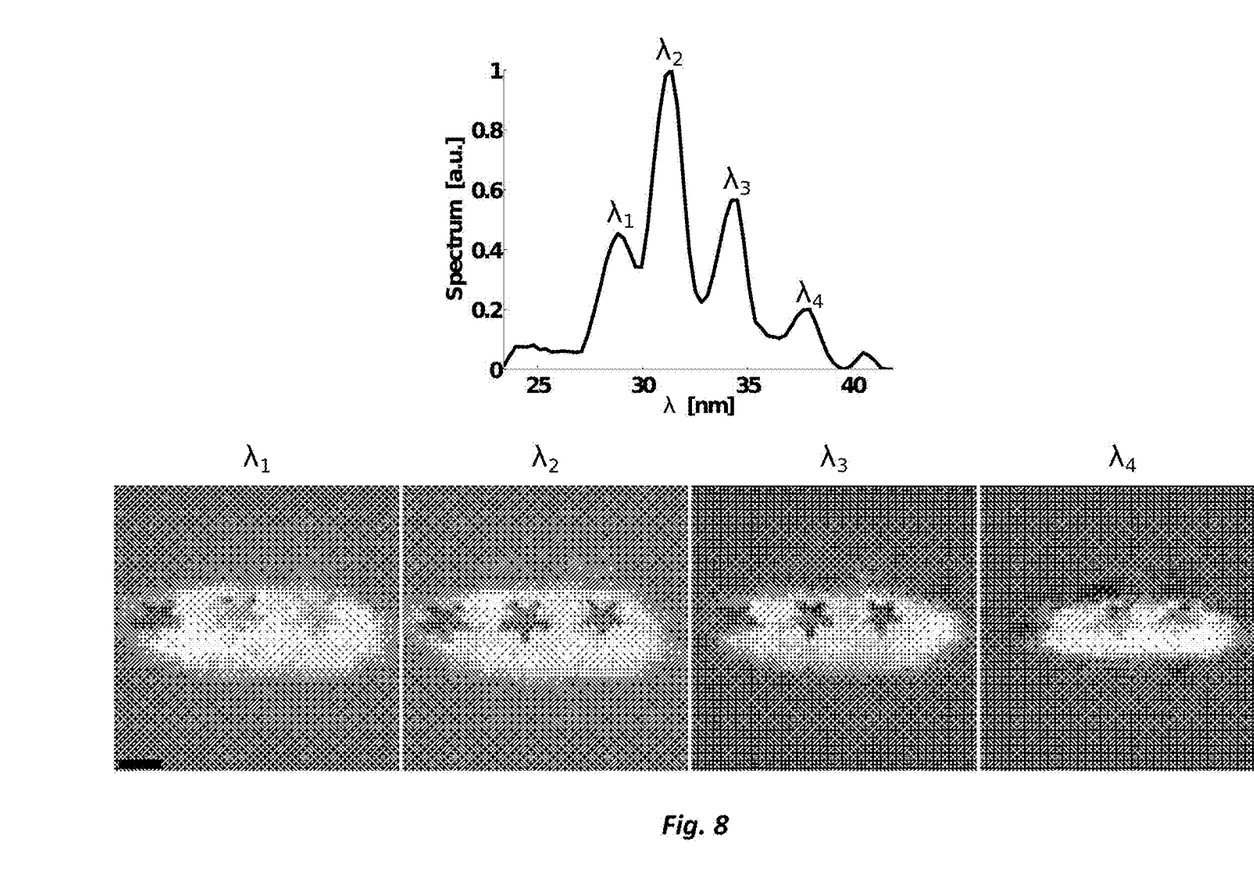
FIG. 8 illustrates hyperspectral imaging using a comb of high-order harmonics.

Imaging using multiple colors in the EUV can be done sequentially; however, it is often more convenient to illuminate the sample with several colors simultaneously, then to use a ptychographic reconstruction to obtain a separate image for each illumination wavelength. FIG. 8 shows the hyperspectral imaging result with a comb of high harmonics (top). The incident illumination contains high harmonics of 4 different wavelengths, $\lambda_1$, $\lambda_2$, $\lambda_3$, $\lambda_4$, as shown in the measured low-resolution spectrum. Multiple harmonics at different wavelengths illuminate the sample at the same time, and the spectral responses at each wavelength are reconstructed separately with the ptychographical information multiplexing (PIM) algorithm (bottom images). This algorithm is used in the prior art Batey, et al., Ultramicroscopy 138, 13-21 (2014) for the visible spectral range; while in this invention we extend this technique to EUV/X-ray range. Imaging at multiple colors can result in elemental selectivity, essentially identifying elements and compound by their "colors" in the EUV/X-ray.

Figure 9A:
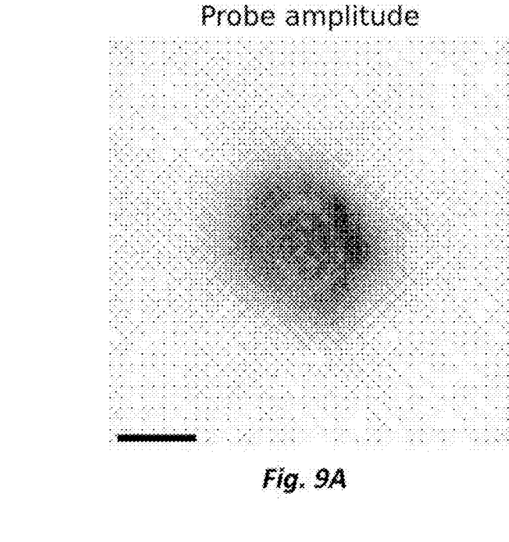
FIGS. 9A-9C illustrate keyhole CDI using the probe reconstructed from ptychography.
Figure 9B:
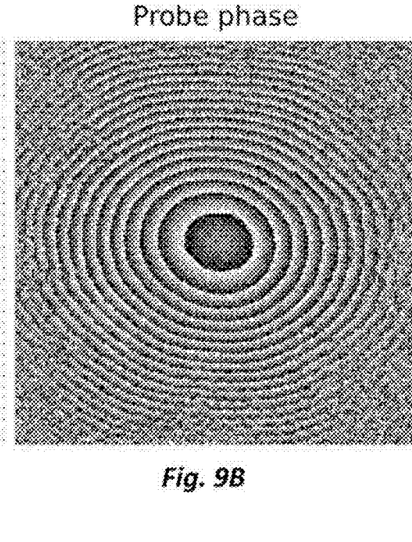
Figure 9C:
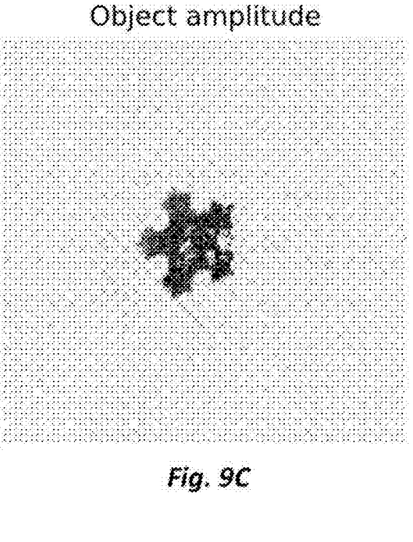

With the probe reconstructed from ptychography, keyhole CDI technique can be employed to reconstruct the sample from a single diffraction pattern. FIGS. 9A-9C illustrate the result of this approach of the invention, with FIG. 9A showing the amplitude and FIG. 9B showing the phase of the probe, and FIG. 9C showing the reconstructed amplitude of the sample.

Due to the ultrashort pulse nature of the HHG light source, embodiments of a microscope of the invention are capable of imaging ultrafast dynamics (changing in time), with temporal resolution of up to femtosecond or even attosecond.

While the embodiments of the present invention have been described hereinabove by way of example with particularity, those skilled in the art will appreciate various modifications, additions, and applications other than those specifically mentioned, which are within the scope of this invention. For example, the fast remapping is applicable not only ptychography CDI, but also other types of CDI.

What is claimed is:

1. A method of Coherent Diffractive Imaging (CDI) with arbitrary angle of incidence comprising the steps of:
   (a) illuminating an object to be imaged with an at least partially-coherent beam to generate a diffractive pattern;
   (b) measuring the diffractive pattern with a detector and generating an amplitude pattern (212) corresponding to an initial detector grid;
   (c) selecting an intermediate spatial grid according to a desired final spatial frequency grid (202), and according to orientation of the object, the detector, and the coherent beam;
   (d) remapping the diffractive field amplitude from the initial detector grid to an intermediate spatial grid to generate remapped pattern.

2. The method of claim 1, further including the step of processing remapped pattern and obtaining imagery.

3. The method of claim 2 wherein the step of processing includes the step of fast Fourier transforming.

4. The method of claim 1 wherein the step of illuminating is accomplished with single wavelength illumination.

5. The method of claim 1 wherein the step of illuminating is accomplished with multi-wavelength illumination.

6. The method of claim 5 wherein the multi-wavelength illumination comprises a comb of high-order harmonics.

7. The method of claim 1 wherein the initial grid is a uniform spatial grid, the intermediate grid is a non-uniform spatial grid, and the final grid is a uniform spatial frequency grid.

8. The method of claim 1 wherein the step of illuminating is accomplished with multi-wavelength illumination.

9. The method of claim 8 wherein step (a) includes the step of high harmonic generation.

10. The method of claim 1 further including the step of ptychography CDI, wherein step (b) measures multiple diffraction patterns.

11. The method of claim 1 further including the step of keyhole CDI, wherein step (a) generates illumination having a curved wavefront.

12. Apparatus for Coherent Diffractive Imaging (CDI) with arbitrary angle of incidence comprising:
   an object;
   an illumination source for illuminating the object with an at least partially-coherent beam;
   a beam modifying element disposed between the illumination source and the object;
   a detector associated with an initial uniform spatial grid for detecting a diffraction intensity pattern from the object; and
   a processor constructed and arranged to remap a pattern based upon the diffraction intensity pattern to an intermediate non-uniform spatial grid based upon a desired final spatial frequency grid and based upon orientations of the object, the detector, and the beam.

13. The apparatus of claim 12, further comprising a vacuum iris far upstream of the optics.

14. The apparatus of claim 12 configured in a transmission configuration.

15. The apparatus of claim 14 configured in a non-normal transmission configuration.

16. The apparatus of claim 12 configured in a reflection configuration.

17. The apparatus of claim 16 configured in a non-grazing reflection configuration.

18. The apparatus of claim 12 wherein the optics includes at least one of the following:
   a grazing incidence focusing optic;
   an off-axis mirror;
   a multi-layer mirror;
   an ellipsoidal mirror;
   a toroidal mirror;
   a spectral filter;
   a zero dispersion stretcher.

19. The apparatus of claim 12 wherein the illumination source provides multi-wavelength illumination.

20. The apparatus of claim 19 wherein the multi-wavelength illumination comprises a range of high-order harmonics.

21. The apparatus of claim 12 configured for ptychography CDI.

22. The apparatus of claim 12 configured for keyhole CDI.

* * * * *

UNITED STATES PATENT AND TRADEMARK OFFICE
CERTIFICATE OF CORRECTION

PATENT NO.         : 9,891,584 B2
APPLICATION NO.    : 14/839738
DATED              : February 13, 2018
INVENTOR(S)        : Bosheng Zhang et al.

Page 1 of 1

It is certified that error appears in the above-identified patent and that said Letters Patent is hereby corrected as shown below:

In the Specification

In Column 1, Line 10, (before "BACKGROUND OF THE INVENTION") insert the following:
-- This invention was made with government support under grant numbers W31P4Q-13-1-0015 awarded by the Defense Advanced Research Projects Agency and EEC-0310717 awarded by the National Science Foundation. The government has certain rights in the invention. --

Signed and Sealed this
Third Day of November, 2020

Andrei Iancu
*Director of the United States Patent and Trademark Office*